Figure 1:
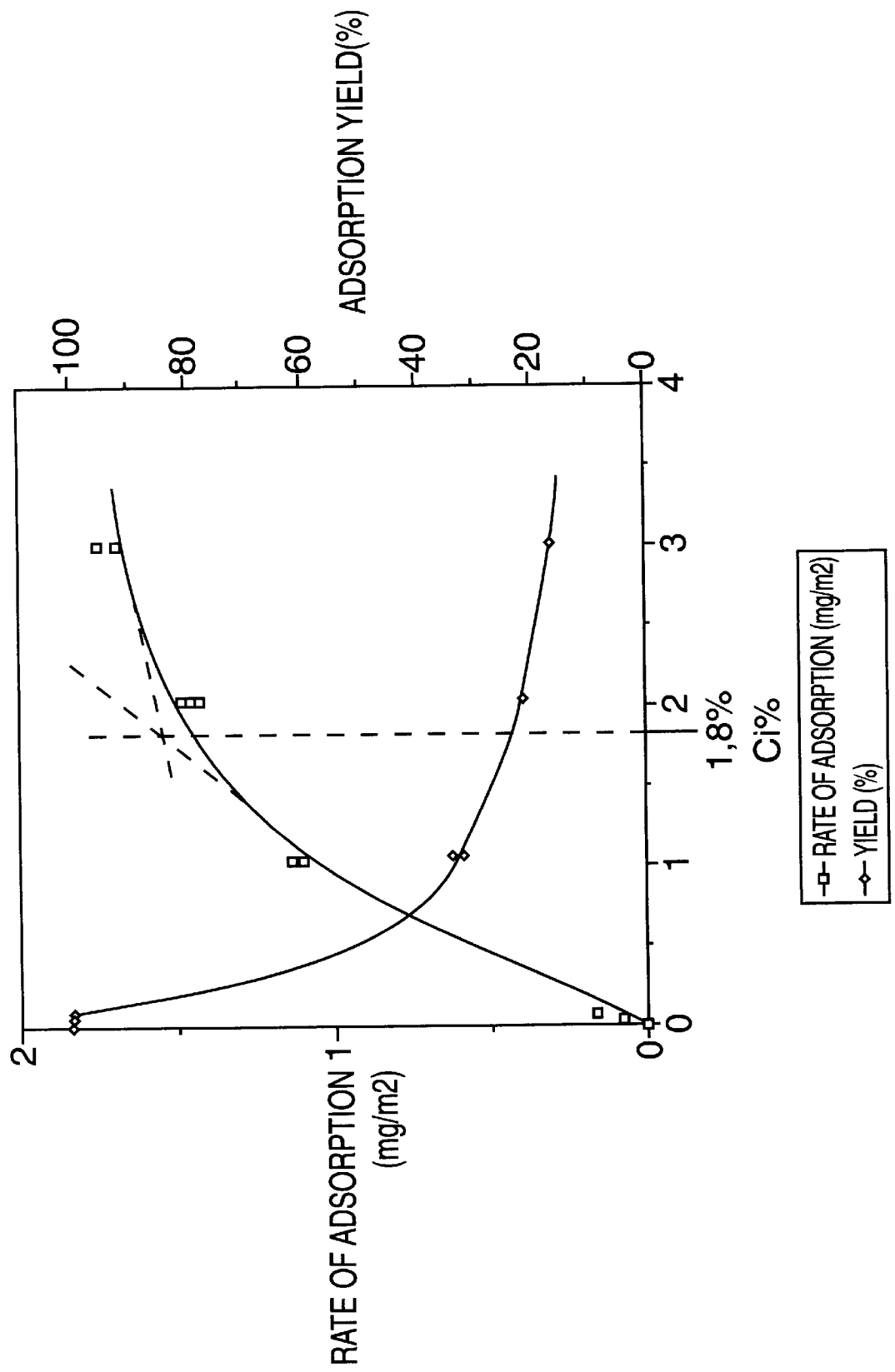
Figure 2A:
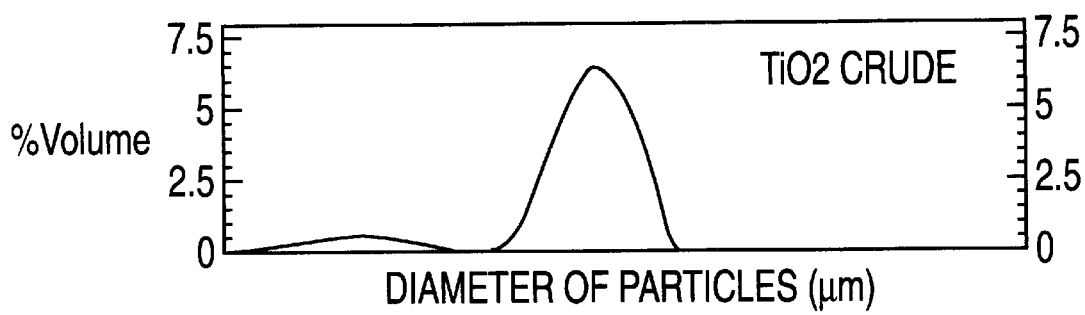
Figure 2B:
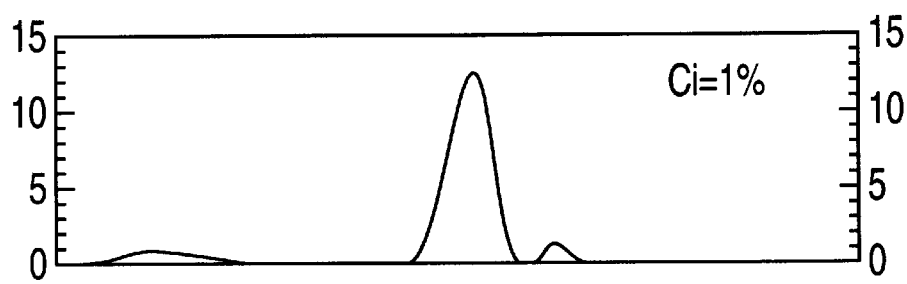
Figure 2C:
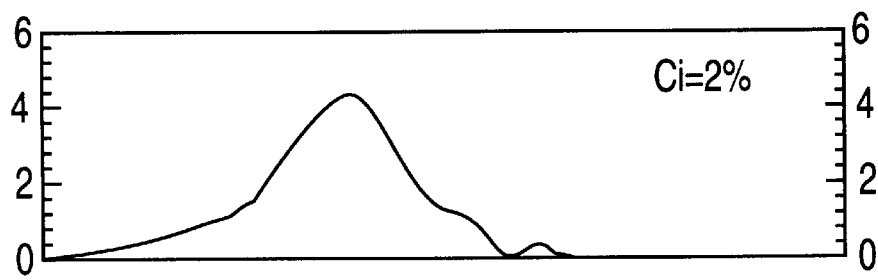
Figure 2D:
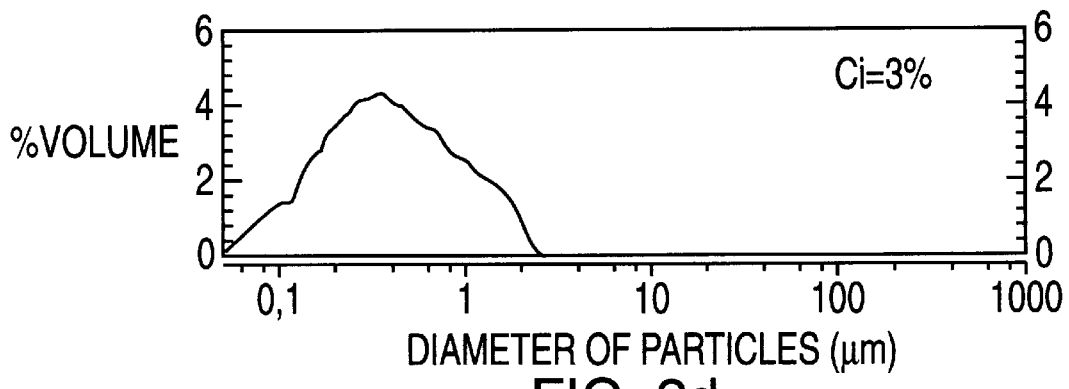

United States Patent
Tondeur et al.

[11] Patent Number: 5,958,385
[45] Date of Patent: Sep. 28, 1999

[54] POLYMERS FUNCTIONALIZED WITH AMINO ACIDS OR AMINO ACID DERIVATIVES, METHOD FOR SYNTHESIZING SAME, AND USE THEREOF AS SURFACTANTS IN COSMETIC COMPOSITIONS, PARTICULARLY NAIL VARNISHES

[75] Inventors: Carole Tondeur; Henri-Gérard Riess, both of Mulhouse; Alain Meybeck, Courbevoie; Jean-Francois Tranchant, Boigny-sur-Bonne, all of France

[73] Assignee: LVMH Recherche, France

[21] Appl. No.: 08/817,386

[22] PCT Filed: Sep. 28, 1995

[86] PCT No.: PCT/FR95/01253

§ 371 Date: Mar. 28, 1997

§ 102(e) Date: Mar. 28, 1997

[87] PCT Pub. No.: WO96/10045

PCT Pub. Date: Apr. 14, 1996

[30] Foreign Application Priority Data

Sep. 28, 1994 [FR] France .................................. 94 11576

[51] Int. Cl.⁶ ............................. A61K 7/043; A61K 7/48; A61K 47/32; B01J 13/00
[52] U.S. Cl. .............................. 424/61; 526/83; 526/287; 526/288; 526/215; 252/314; 252/356; 252/358; 514/772.4; 514/772.6
[58] Field of Search ..................... 526/287, 288, 526/83, 215; 252/357, 358

[56] References Cited

U.S. PATENT DOCUMENTS 3,684,771 8/1972 Braun .
3,689,593 9/1972 Jackson .

(List continued on next page.)

FOREIGN PATENT DOCUMENTS 160103 11/1985 European Pat. Off. .
207026 12/1986 European Pat. Off. .

(List continued on next page.)

OTHER PUBLICATIONS

C. Erbil et al., "The Free–Radical Polymerizatio of Acrylamide Initiated with Ceric Sulfate in the Presence of Amino Acids" *Die Angewandte Makromolekulare Chemie* 213 (1993) 55–63, Nr. 3693.

(List continued on next page.)

*Primary Examiner*—Peter F. Kulkosky
*Attorney, Agent, or Firm*—Bierman, Muserlian and Lucas

[57] ABSTRACT

The invention relates to a chain end functionalised polymer of formula:

$$(P)-\underset{\underset{COOH}{|}}{\overset{\overset{R}{|}}{C}}-A-NH_2 \tag{1}$$

in which:

the polymer chain (P) is a hydrophobic chain obtained by radical polymerisation of at least one monomer, R represents a hydrogen atom or a linear or branched hydrocarbon chain having 1 to 8 carbon atoms optionally substituted with at least one group selected from $CO_2$, $NH_2$, OH or a phenyl group, itself being optionally substituted, A and B, identical or different, each represent a single bond, a saturated or unsaturated linear or branched hydrocarbon chain having from 1 to 16 carbon atoms, it being possible for it to contain an amide bond or a peptide chain having 2 to 4 amino acids, particularly natural amino acids, the $NH_2$ and/or COOH groups being free or salified.

The invention also relates to the use of the above products as surfactants and more particularly as wetting agents, dispersing agents of solid particles and for preparing microdispersions of polymers, in particular microgels and microlatexes. The invention also relates to cosmetic compositions incorporating these products and notably nail varnishes.

41 Claims, 10 Drawing Sheets

U.S. PATENT DOCUMENTS

| | | |
|---|---|---|
| 3,788,996 | 1/1974 | Thompson . |
| 3,806,464 | 4/1974 | Matrick et al. .......................... 252/314 |
| 4,032,698 | 6/1977 | Ashe . |
| 4,070,388 | 1/1978 | Jones . |
| 4,107,096 | 8/1978 | McEntire et al. . |
| 5,298,585 | 3/1994 | McCallum, III et al. . |
| 5,384,372 | 1/1995 | Lattime ...................................... 526/83 |
| 5,412,051 | 5/1995 | McCallum, III et al. ........... 526/317.1 |
| 5,631,336 | 5/1997 | Ferroti et al. ............................ 526/264 |

FOREIGN PATENT DOCUMENTS

| | | |
|---|---|---|
| 1545883 | 12/1969 | Germany . |
| 3643792 | 6/1988 | Germany. |

OTHER PUBLICATIONS

G. Mino et al.—"The Polymerization of Acrylamide Initiated by Ceric Nitrate–3–Chloro–1–Propanol Redox Systems" —J. Polymer Science—vol. XXXVIII, pp. 393–401 (1959).

S.V. Subramanian et al. —"Vinyl Polymerization Initiated by Ceric Ion Reducing Agent Systems in Sulfuric Acid Medium" —Journal of Polymer Science —Part A–1, vol. 6, 493–504 (1968).

A. Sezai Sarac et al. —"Polymerization of Acrylamide Initiated with Electrogenerated Cerium (IV) in the Presence of EDTA" —Journal of Applied Polymer Science, vol. 44, 877–881 (1992).

E. Goethals, "Telechelic Polymers Synthesis and Applications" CRC Press, (1989), pp. 169–179.

C. Erbil et al., The Free–Radical Polymerication of Acryla-Mide Initiated with Ceric Sulfate in the Presence of Amino Acids, Die Angewandte Makromolekulare Chemie 213, (Nr. 3693), (1993), 55–63.

H. Jakubauskas, "Use of A–B Block Polymers as Dispersants for Non–Aqueous Coating Systems", J. Coat Techn. 58, N. 736, (1986), 71–82.

POLYMERS FUNCTIONALIZED WITH AMINO ACIDS OR AMINO ACID DERIVATIVES, METHOD FOR SYNTHESIZING SAME, AND USE THEREOF AS SURFACTANTS IN COSMETIC COMPOSITIONS, PARTICULARLY NAIL VARNISHES

The present invention relates to novel functionalised polymers, method for synthesising same and uses thereof as surfactants, especially as wetting agents and/or dispersing agents and/or stabilising agents of dispersions of solid particles, and for preparing microdispersions.

Chain end-functionalised polymers are already known and, more particularly, functionalised polymers obtained by polymerisation in the presence of a chain transfer agent.

More particularly, work in this field by Y. YAMASHITA, Y. CHUJO and al. will be cited. The authors have essentially described the synthesis of methyl polymethacrylates (PMMA) having —OH or —COOH end groups obtained by using thiomalic acid as chain transfer agent, together with their use in the preparation of macromonomers and as macromonomers for polycondensations.

These pieces of work are stated in "Telechelic Polymers Synthesis and Applications" E. J. GOETHALS, CRC Press Inc. (1989) 169–179.

Macromonomers of general formula (PMMA) SCH (COOH)CH$_2$COOH, as well as other acrylic macromonomers having the same end function, are described by Y. YAMASHITA, Y. CHUJO, H. KOBAYASHI and KAWAKAMI in Polym. Bull., 5, 361–366 (1981). All these macromonomers are intended for use in polycondensation operations.

Macromonomers which are also intended for polycondensation operations are described by Y. CHUJO, H. KOBAYASHI and Y. YAMASHITA in J. of Polym. Sci., Part A: Polym. Chem., 27, 2007–2014 (1989), these macromonomers being constituted of a polymer PMMA chain with a dicarboxylic aromatic functional end group.

In all these documents, the functionalised macromonomers are used as reaction intermediate products in the preparation of other macromonomers, or directly as macromonomers for carrying out polycondensation or coupling reactions.

U.S. Pat. No. 3,689,593 describes graft copolymers in which the grafts are constituted of macromonomers with an OH, COOH or NH$_2$ end group, with which a diisocyanate, and then a functional vinylic monomer have reacted. These polymers are useful as filmogenic agents in compositions such as paints.

Other macromonomers in which the functional group is linked to the polymer group by an isocyanate group have been described particularly for their application in the dispersion and stabilisation of pigments. The following references shall most particularly be cited:

H. L. JAKUBAUSKAS in J. Coat. Techn., 58, n° 736, 71–82 (1986),

F. N. JONES in U.S. Pat. No. 4,070,388,

T. A. ASHE in U.S. Pat. 4,032,698,

D. R. THOMPSON in U.S. Pat. No. 3,788,996, and

R. A. BRAUN in U.S. Pat. No. 3,684,771.

The compounds described in the various documents above are constituted of various types of polymer chains functionalised with various end groups. All these macromonomers are obtained by functionalising a polymer chain with, for example, an —OH group with which a triisocyanate then reacts. A polymer chain is thus obtained which has two isocyanate end groups with which thiomalic acid may then be grafted. The dispersions carried out by the intermediate of these compounds are extremely resistant to flocculation, giving paintings in which they are incorporated increased covering capacity, brightness as well as improved resistance to loss of brightness. Moreover, the proportion of pigments may be increased in keeping the same degree of fluidity as with conventional dispersing agents. However, these products contain isocyanates which can prove to be a nuisance in a cosmetic formulation if there are residual isocyanate functions.

Polymers functionalised at their chain ends with an amino acid have been described by Candan Erbil, Bahattin Soydan, A. Zehra Aroguz and A. Segai Saraç in Angewandte Makromolekulare Chemie 213, (1993), 55–63, (Nr 3693).

These polymers are obtained by radical polymerisation of acrylamide in an acid medium initiated by cerium sulphate in the presence of an α-amino acid. The pieces of work described in this publication result from older pieces of work described in the publications below:

G. MINO, S. KAIZERMAN and E. RASMUSSEN J. Polym. Sci., Vol. XXXVIII, 393–401 (1959)

S. V. SUBRMANIAN and M. SANTAPPA J. Polym. Sci., Part A-1, 6, 493–504 (1968)

A. SEZAI SARAC, CANDAN ERBIL and A. BAHATTIN SOYDAN J. Appl. Polym. Sci., 44, 877–881 (1992)

Hence, the process described in Candan Erbil, Bahattin Soydan, A. Zehra Aroguz and A. Segai Saraç in Angewandte Makromolekulare Chemie 213, (1993), 55–63, necessitates the use of concentrated solutions of acid (sulphuric acid, nitric acid, ... or perchloric acid), therefore a medium which is unfavourable for most amino acid derivatives. Furthermore, in Candan Erbil, Bahattin Soydan, A. Zehra Aroguz and A. Segai Saraç only describe the synthesis of products with a hydrophobic polymer chain which do not therefore have a surfactant character.

Furthermore, U.S. Pat. No. 5,298,585 describes products of dispersant character which are constituted of polymers functionalised on their chain ends with an amine sulphide. The patent shows the superiority of these products compared to analogous products which are, as for them, functionalised by a product of the amino acid type. However, all the products described in this document, which are products necessarily soluble in water, are products constituted of an essentially hydrophilic polymer chain and a polar head and owe their dispersant properties to only the polarity of this head.

Consequently, the products described in this document, just as those described in the article cited prior to Candan Erbil et al., do not have any surfactant properties.

The applicant has now found novel polymers which are functionalised with amino acids or amino acid derivatives and which have a hydrophobic polymer chain.

These products have the advantage of having remarkable surfactant properties which enables their use in particular as wetting agents for surfaces or solid particles, and/or dispersing agents and/or stabilising agents of dispersions of solid particles in an organic medium, as well as for the preparation of microdispersions of polymers in particular for the preparation of microgels or microlatexes.

Thus, according to one of the essential characteristics, the invention relates to a chain end-functionalised polymer of formula:

$$(P)-\underset{\underset{COOH}{|}}{\overset{\overset{R}{|}}{C}}-A-NH_2 \quad (1)$$

in which:
the polymer chain (P) is a hydrophobic chain obtained by radical polymerisation of at least one monomer,
R represents a hydrogen atom or a linear or branched hydrocarbon chain having 1 to 8 carbon atoms optionally substituted with at least one group selected from $CO_2H$, $NH_2$, OH or a phenyl group, itself being optionally substituted,
A and B, identical or different, each represent a single bond, a saturated or unsaturated linear or branched hydrocarbon chain having from 1 to 16 carbon atoms, it being possible for it to contain an amide bond or a peptide chain having 2 to 4 amino acids, particularly natural amino acids,
the $NH_2$ and/or COOH groups being free or salified.

In the functionalised polymers defined above, the polymer chain (P) has advantageously a number average molar mass between 500 and 250,000.

Generally, the products of formula (1) of the invention may be obtained by radical polymerisation of at least one monomer leading to the formation of the hydrophobic polymer chain (P) in the presence of an amino acid or an amino acid derivative of formula (2) below:

$$H-\underset{\underset{COOH}{|}}{\overset{\overset{R}{|}}{C}}-A-NH_2 \quad (2)$$

acting as chain transfer agent during said radical polymerisation.

In the formula (2) above, the R, A and B groups have the meanings given for the same groups in formula (1).

The role of the chain transfer agent of the product of formula (2) in the radical polymerisation is rendered possible due to the labile character of the hydrogen carried by the carbon in the formula (2) above.

This method, which uses an amino acid or an amino acid derivative as chain transfer agent during the radical polymerisation of at least one monomer leading to the formation of a polymer chain (P), is inspired by analogy to the method described in the pieces of work by Y. YAMASHITA, Y. CHUJO et al., cited above, in replacing the thiol with an amino acid or an amino acid derivative having a labile hydrogen atom.

More specifically, as it has been pointed out above, the synthesis of PMMAs functionalised with carboxylic acid groups is already known. YAMASHITA, CHUJO et al. have developed this type of macromonomers with the aim of copolymerising them by copolymerisation and thus forming graft copolymers (see particularly, E. J. GOETHALS, "Telechelic Polymers Synthesis and Applications" CRC Press, Inc, 169–179 (1989)).

The principle of this synthesis consists of radical polymerising methyl methacrylate in the presence of a transfer agent bearing acid functions, in this case thiomalic acid, under the conditions indicated in the reaction scheme (I) below:

$$CH_2=C\begin{matrix}CH_3\\COOCH_3\end{matrix} \xrightarrow[CH_2COOH]{HSCHCOOH} \text{(I)}$$

This reaction is carried out in a solvent medium, e. g. THF, in the presence of a radical polymerisation initiator, e. g. azobisisobutyronitrile (AIBN), at a temperature in the order of 60° C.

It will be possible for the functionalised polymers according to the invention to be advantageously prepared by an analogous method inspired from the reaction scheme (1) above by selecting the monomer(s) and the amino acid or the amino acid derivative according to the final product sought-after.

The radical polymerisation reaction of the monomer(s) will be carried out in a solvent medium in the presence of a radical polymerisation agent constituted of an organo-soluble initiator preferably selected from the family of azo initiators.

Azobisisobutyronitrile (AIBN) will be cited as an example of a preferred initiator.

The reaction takes place in a solvent medium.

The solvent or the mixture of solvents will be selected according to the nature of the monomer(s) to be polymerised and the amino acid or the amino acid derivative used.

The solvent or the mixture of solvents will be selected according to the nature of the reagents. Preferably, it will be a matter of a solvent or a mixture of solvents which is capable of dissolving the whole of the reagents present, namely the monomers, the polymer formed, the initiator and the transfer agent.

The solvent may have an acidic character, acetic acid will be used for example; it may also have a basic character, e.g. dimethylethanolamine.

The reaction temperature will advantageously be between 30° C. and 120° C., but is to be adjusted according to the reagents present. It is easily understood that it depends on the nature of the initiator and the nature of the solvent.

The molecular mass of the functionalised polymer resulting from the process described above will be controlled in adjusting the amount of chain transfer agent introduced.

The proportions of initiator, transfer agent and monomer (s) may be calculated according to the classical relationship known for chain transfer:

$$\frac{1}{DPn} = \frac{1}{DPn_0} + Cs\left(\frac{S}{M}\right)$$

wherein
S/M is the chain transfer agent/monomer molar ratio to be applied,
Cs is the transfer constant depending on the nature of the monomer(s), the transfer agent, the temperature and the solvent, DPn is the degree of polymerisation of the polymer that is desired to be synthesised, DPn$_0$ is the degree of polymerisation of the polymer that would have been obtained in the absence of a transfer agent.

Hence, according to another of its aspects, the invention relates to a method of preparing functionalised polymers according to the invention which consists of carrying out the radical polymerisation of a monomer leading to a hydrophobic polymer chain (P) in the presence of an amino acid or an amino acid derivative acting as a chain transfer agent during the radical polymerisation and of formula (2)

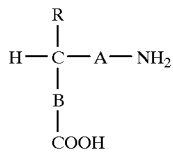

(2)

in which:

R represents a hydrogen atom or a linear or branched hydrocarbon chain having 1 to 8 carbon atoms optionally substituted with at least one group selected from CO$_2$H, NH$_2$, OH or a phenyl group, itself being optionally substituted, A and B, identical or different, each represent a single bond, a saturated or unsaturated linear or branched hydrocarbon chain having from 1 to 16 carbon atoms, it being possible for it to contain an amide bond or a peptide chain having 2 to 4 amino acids, particularly natural amino acids.

Hence, as examples of interesting products according to the invention, the products of the following formulae will be cited:

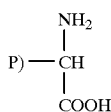

(3)

obtained by using glycine H$_2$N—CH$_2$—COOH as chain transfer agent,

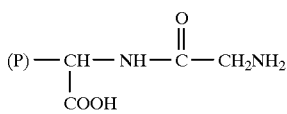

(4)

and

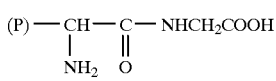

(5)

obtained by using glycylglycine,

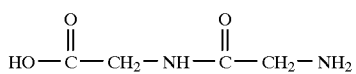

as chain transfer agent, this product having two carbons which bear relatively labile hydrogens.

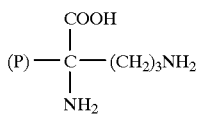

(6)

obtained by using ornithine

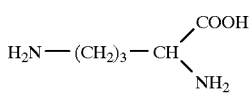

as chain transfer agent.

A sub-family of products according to the invention corresponds to products of formula (7) below:

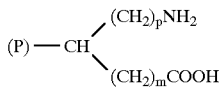

(7)

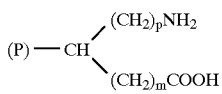

(7)

in which

P indicates a hydrophobic polymer chain obtained by radical polymerisation of at least one monomer, m and p are integers between 0 and 11 and whose sum is between 2 and 11.

These products of formula (7) are advantageously prepared by a method consisting of:

a radical polymerisation step of at least one monomer leading to a hydrophobic polymer chain (P) in the presence of a lactam acting as chain transfer gent and being of formula (8):

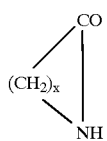

(8)

in which x is an integer between 3 and 12, followed by a second hydrolysis step of the product obtained during the first step.

The intermediate product resulting from the first step of the method above is itself patentable in itself as a novel intermediate product.

Such a product is of formula (9):

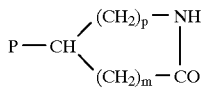

(9)

in which:
P is a hydrophobic polymer chain resulting from the radical polymerisation of at least one monomer,
p and m are integers between 0 and 11 and whose sum is between 2 and 11.

In all the polymers described above, it will be possible for the polymer chain (P) to be constituted of any hydrophobic polymer chain obtainable by radical polymerisation of at least one monomer.

It will therefore be a matter of both a chain constituted by radical polymerisation of one sole type of monomer and a chain constituted by radical polymerisation of a mixture of several different monomers.

An acrylic or vinylic monomer will advantageously be selected as monomer.

Amongst the acrylic monomers, the acrylates, methacrylates and ethylacrylates of a saturated or unsaturated particularly allylic, linear, branched, or ring-containing, C1 to C18 hydrocarbon group, will most particularly be cited.

A preferred monomer according to the invention is methyl methacrylate. The polymer chain will then be constituted of methyl polymethacrylate (PMMA).

Amongst the vinylic monomers, styrene, alpha-methyl styrene, substituted styrenes, acrylonitrile, vinylic esters such as vinyl acetate will notably be cited.

Amongst the mixtures of monomers, mixtures of alkyl acrylate or methacrylate and allyl acrylate or methacrylate will be particularly cited, more particularly mixtures of methyl methacrylate and allyl methacrylate. The advantage of such monomers is that they lead to partially unsaturated polymer chains which enable obtaining specific properties of the polymers linked to the presence of these unsaturated bonds in the polymer chain.

As it has been seen above, the length of the chain may be adjusted by adjusting especially the proportion of thiol acting as chain transfer agent.

However, the most interesting compounds according to the invention are those for which the polymer chain (P) has a number average molar mass between 500 and 250,000.

All the above functionalised polymers above have interesting surfactant properties.

More specifically, all the functionalised polymers described above enable, due to their surfactant properties, lowering surface or interfacial tension, which is a matter of a liquid/liquid or a liquid/solid system.

In particular, these products, when placed in contact with a surface, enable lowering its surface energy.

These products, when placed in the presence of a particulate load, also enable lowering the surface energy of said particles. This phenomenon of lowering the surface energy of the particles manifests itself as a wetting effect of the polymer with respect to said particle, by a dispersing effect of said particles when these particles are in suspension in a solvent, and by a stabilising effect of the dispersions of particles in a solvent.

For these different types of surfactant effects in the liquid/solid systems, the functionalised polymers may be salified or not.

The surfactant properties of the functionalised polymers described above may also manifest themselves in liquid/liquid systems.

As examples of such liquid/liquid systems, oil-in-water emulsions, water-in-oil emulsions may be cited as well as systems constituting starting systems intended to be polymerised for preparing a latex.

In the case of these liquid/liquid systems, the functionalised polymer may be either in the salified form or in the free form, but it will be preferably in the salified form, which increases its emulsifying potential.

Hence, all the above functionalised polymers have interesting surfactant properties enabling in particular their use as wetting agents and/or dispersing agents and/or stabilising agents for solid particle dispersions, enabling thus the formation of stable dispersions of particles.

Moreover, these same functionalised polymers, after neutralisation if need be of the COOH and $NH_2$ groups, have interesting surfactant properties, which enable in particular their use for preparing microdispersions of polymers in particular in the form of microlatex and microgels.

Hence, according to another of its aspects, the invention relates to the use of a functionalised polymer of formula (1) such as defined above and in which the hydrophobic polymer chain (P) has a number average molar mass between 500 and 250,000, as surfactants.

The applicant has most particularly demonstrated the surfactant properties of the functionalised polymers defined above by studying their effect on the surface energy of a solid, particularly a particle.

The applicant has also demonstrated their wetting character as well as their dispersing and stabilising properties of dispersions of particles.

The applicant's studies have led, for the various functionalised polymers of the family, according to the nature of the medium in which it is desired to disperse the powder as well as the nature of the powder:

on the one hand, to the determination of the adsorption yield of the functionalised polymer defined as the amount of functionalised polymer <fixed> with respect to the amount employed. <Fixed> functionalised polymer meaning the functionalised polymer adsorbed by the physical bonds on the surface of the solid particle, and on the other hand, to the determination of the efficiency of the surfactant as a wetting agent and/or dispersing agent and/or stabilising agent.

The applicant's studies have in particular brought about the demonstration of the existence of a plateau in the curves, known as adsorption isotherms, which represent the rate of adsorption of the functionalised polymer according to the initial concentration of the functionalised polymer at a given temperature.

The efficiency of the wetting agent and/or dispersing agent and/or stabilising agent is characterised by the minimal amount of functionalised polymer to be employed in order to reach the adsorption isotherm plateau and to cover all the surface of the particle.

The applicant's studies have led to the demonstration of the significant reduction of the wettability parameter of the solid particles. This effect demonstrates the wetting character of the products according to the invention.

Hence, the invention also relates to the use of the surfactants defined above as a wetting agent of a solid surface or a solid particle.

The applicant has also demonstrated the significant reduction of the amount of aggregates formed between the particles and/or the significant reduction in their size in the presence of functionalised polymer in the medium. This effect demonstrates the dispersant character of the products according to the invention.

The invention also relates therefore to the use of the functionalised polymers of the family (1) in which the number average molar mass of the polymer chain is between 500 and 250,000 as dispersing agents of solid particles in an organic medium.

The applicant has also demonstrated that the functionalised polymers defined above constituted remarkable stabilising agents of dispersions of solid particles in organic media and enabled in particular obtaining dispersions whose supernatant does not become limpid before at least 24 hours for the contents of polymers which correspond to the plateau of the adsorption isotherm.

The solid particles may be of any type and have advantageously dimensions between a few nanometers and a few millimeters, preferably between 50 nm and 100 $\mu$m.

It may also be a matter in particular of inorganic particles, particularly of metallic oxide particles, for example $TiO_2$, $SiO_2$, $Al_2O_3$, iron oxides such as goethite, haemetite or magnetite.

It may also be a matter of metallic oxide particles covered with organic colorant molecules.

It may also be a matter of organic particles, for example of the rosinate type, co-precipitated with an organic colorant.

The organic medium used for carrying out the treatment of the solid particles may be any solvent of the polymer chain (P).

As an example, when the polymer chain is constituted of PMMA, the solvent will advantageously be selected from the esters such as methyl, ethyl, butyl or amyl acetates, ketones such as acetone, methyl ethyl ketone or cyclohexanone, chlorinated solvents such as chloroform or dichloromethane, or others such as toluene, and acetic acid.

It will also be possible to use mixtures of a solvent of PMMA with a non-solvent of PMMA in proportions which keep these sequence soluble, such as, for example, a butyl acetate/ethanol or isopropanol mixture which contains at least 50% butyl acetate.

All the functionalised polymers described above have a wetting and dispersing effect.

The stabilising effect of the dispersion itself is only noticeable as from a number average molecular mass of the polymer which is greater than 1,000, preferably between 5,000 and 150,000.

However, it will easily be understood that the values depend upon both the nature of the filler to be dispersed as well as that of the polar head of the functionalised polymer.

The invention can be applied most particularly to the dispersion of titanium oxide particles, particularly particles of dimensions between 50 nm and 1 $\mu$m.

In practice, the adsorption yield is determined in the following way: a mass $m_s$ of solution of initial polymer concentration Ci is placed in contact with a mass $m_c$ of particles of specific surface S. After adsorption, and after the removal of the particles by centrifugation, the new concentration (Ce) of the solution is determined. The yield (r) is given by the formula:

$$r=(Ci-Ce)/Ci\times100(\%)$$

The rate of adsorption (t) itself is given by:

$$t=[(Ci-Ce)\times m_s]/m_c\times S$$

The dispersability is evaluated from the measurements of the sizes of the particles, for example with the aid of an apparatus of the Coulter LS130 type.

A particular advantage of the functionalised polymers used as dispersants according to the invention is that they lead to stable dispersions.

Hence, according to one of its aspects, the invention relates to stable dispersions of solid particles in a solvent, or a mixture of solvents, in which the dispersing agent is a functionalised polymer of formula (1) such as defined above and of number average molar mass between 500 and 250,000, said solvent or mixture being a solvent of said polymer chain.

The stabilisation of the dispersions is appreciated either by measuring the speed of sedimentation of the suspensions with time, or by following the variations of the absorbance of the supernatant with the duration of the centrifugation.

One advantage of the dispersions according to the invention is that, when a decantation is produced with time, the deposit formed remains easily redispersable in the medium after stirring, the polymer totally covering the surface of the particle, which thus prevents its aggregation.

Another advantage of the dispersions according to the invention is that, when they are dried at room temperature, the powder recovered can be easily redispersed later in the solvent.

According to another of its essential characteristics, the invention also relates to any composition which contains the dispersions described above. It relates most particularly to the compositions which contain dispersions of pigments intended for the cosmetics field.

All the products described above as wetting agents and/or dispersing agents and/or stabilising agents of dispersions of particles may also be used as surfactants having the emulsifying role after neutralisation, if need be, of the COOH or $NH_2$ groups.

The invention also relates to the use of the same polymers for the preparation of microdispersions of polymers:
either in aqueous or aqueous-alcohol media (as we shall refer to as microlatex),
or in organic media (which we shall refer to as microgels) thus demonstrating their surfactant properties.

For this application, from the functionalised polymers defined above, those having a number average molecular mass ($M_n$) lower than about 20,000, preferably between 500 and 10,000, will be preferably selected.

Due to their surfactant properties, the useful functionalised polymers according to the invention can easily form micellar solutions in aqueous media, after neutralisation of their acid and/or basic functions.

These micellar solutions can then be used in the formulation of latexes, in particular cross-linked latexes, notably cross-linked latexes of small sizes referred to as microlatexes (10–150 nm). These microlatexes may be prepared by any polymerisation method in emulsion in the presence of an organo or hydrosoluble initiator, as it has been shown by W. FUNKE with saturated or unsaturated polyesters, particularly in:

"Emulsifying properties of saturated polyesters" H. BAUMANN, B. JOOS, W. FUNKE, Makromol. Chem., 187, 2933 (1986), "Saturated polyesters as emulsifiers for emulsion copolymerization of unsaturated polyester resins with styrene" H. BAUMANN, B. JOOS, W. FUNKE Makromol. Chem., 190, 83–92 (1989), "Reactor Microgels by Self-emulsifying Copolymerization of Unsaturated Polyester Resins with Acrylic and Methacrylic Esters" Makromol. Chem., 184, 755–762 (1983) M. MIYATA, W. FUNKE "Reactive Microgels by Emulsion Polymerization of Unsaturated Polyester Resins" Y.-Ch. YU, W. FUNKE Die Angewandte Makromol. Chem., 103, 187–202 (1982), "Surfactant Properties of Unsaturated Polyesters" Y.-Ch. Yu, W. FUNKE Die Angewandte Makromol. Chem., 103, 203–215 (1982).

The advantage of these microlatexes is that:

they give very stable polymer dispersions, once dry, powders of extremely high specific surfaces are obtained;

they enable preparing microgels;

they also enable forming films (according to the nature of the polymer and the solvent).

These microlatexes may then advantageously be used for the preparation of microgels.

These microgels are obtained from the above cross-linked microlatexes, either by transferring the particles constituting the dispersion in a solvent after prior drying the dispersion, or by azeotropic removal, or by mixing with a solvent and then distilling the water.

As examples of solvents, the aromatic solvents will be cited, the chlorinated solvents such as chloroform or methylene chloride, ketones and esters such as $C_2$ to $C_4$ alkyl acetates, more particularly butyl acetate and ethyl acetate.

The microgels of the invention prove to be particularly useful in the cosmetic and paints fields, where they enable adjusting the rheological characteristics. It is in fact possible to mix the microgels with formulations based on nitrocellulose of high dry extract, without especially increasing the viscosity of the system which results from it.

The fact that the products are compatible with the nitrocellulose dissolved in butyl acetate giving a transparent and bright film enables envisaging their use for making varnishes, particularly nail varnishes.

More specifically, the use of the microgels of the invention in the formulations of varnishes and particularly nail varnishes has the following advantages:

it enables improving the rheological properties which enables, in particular, avoiding the precipitation of the pigments, and an improvement of the reproducibility of these properties. This enables , in particular, to appreciably decrease, even to do away with, the amount of organophilic clays generally used to this end but whose disadvantages are well-known, it enables increasing the dry extract of the film constituted by the varnish without meaning appreciably increasing the viscosity of the varnish;

it confers more brightness to the film, it reinforces the thixotropic effect brought about by the organophilic clay in acetate medium.

The weight proportion of microgel according to the invention, in the final composition of the varnish, may rise up to about 30%, for example in the case where it would be sought to lower, even to do away with the quantity of nitrocellulose. However, in general it is preferred to use proportions between about 1 and 20% by weight.

As it arises from the preceding account, the dispersions of particles described above as well as the microgels may advantageously be introduced in different compositions, especially cosmetic compositions and in particular nail varnishes.

Hence, according to other aspects, the invention also relates to compositions, especially cosmetic compositions which contain functionalised polymers according to the invention.

In particular, these cosmetic compositions are intended for the care or the make-up of the nails and contain dispersions of particles, particularly pigments, described above.

The invention also relates to microlatexes and microgels described above as well as the compositions, especially the cosmetic compositions containing them.

It relates most particularly to the compositions which further contain nitrocellulose, particularly nail varnishes.

More generally, it also relates to the use of the polymers of the family (1) for the preparation of a composition, particularly a composition of the paint type, or a food composition, a phytosanitary composition or a cosmetic composition, particularly a cosmetic composition intended for the care or the make-up of the nails and more particularly a nail varnish.

The invention relates most particularly, as this arises from the preceding account, to the use of the polymers defined above for the preparation of compositions which contain solid particles in suspension, particularly pigments, in which said functionalised polymer is placed in the presence of said solid particles, especially said pigments, in order to facilitate their dispersion in the composition.

In the compositions described above, the amount of functionalised polymers used is advantageously between 2% and 7% by weight with respect to the total weight of the solid particles dispersed in the composition.

In the compositions defined above, the functionalised polymer is advantageously comprised in polymer microdispersions, especially microgels or microlatexes, the functionalised polymer being like it has been shown before used as a surfactant for the preparation of these microgels or microlatexes.

The amount of microdispersions of polymers, microgels or microlatexes is advantageously between 1% and 20% by weight with respect to the total weight of the composition.

According to a last aspect, the invention relates, as this arises from the preceding account, to cosmetic compositions, and, most particularly, to cosmetic compositions intended for the care or the make-up of the nails, which contain functionalised polymers defined above, in particular comprised in microdispersions, especially microlatexes or microgels.

It relates most particularly to cosmetic compositions which further contain nitrocellulose.

EXAMPLES

Examples which are purely illustrative of the invention are given below.

They are given with reference to FIGS. 1 to 10 which illustrate the dispersant and stabilising properties of the products.

Figure 3:
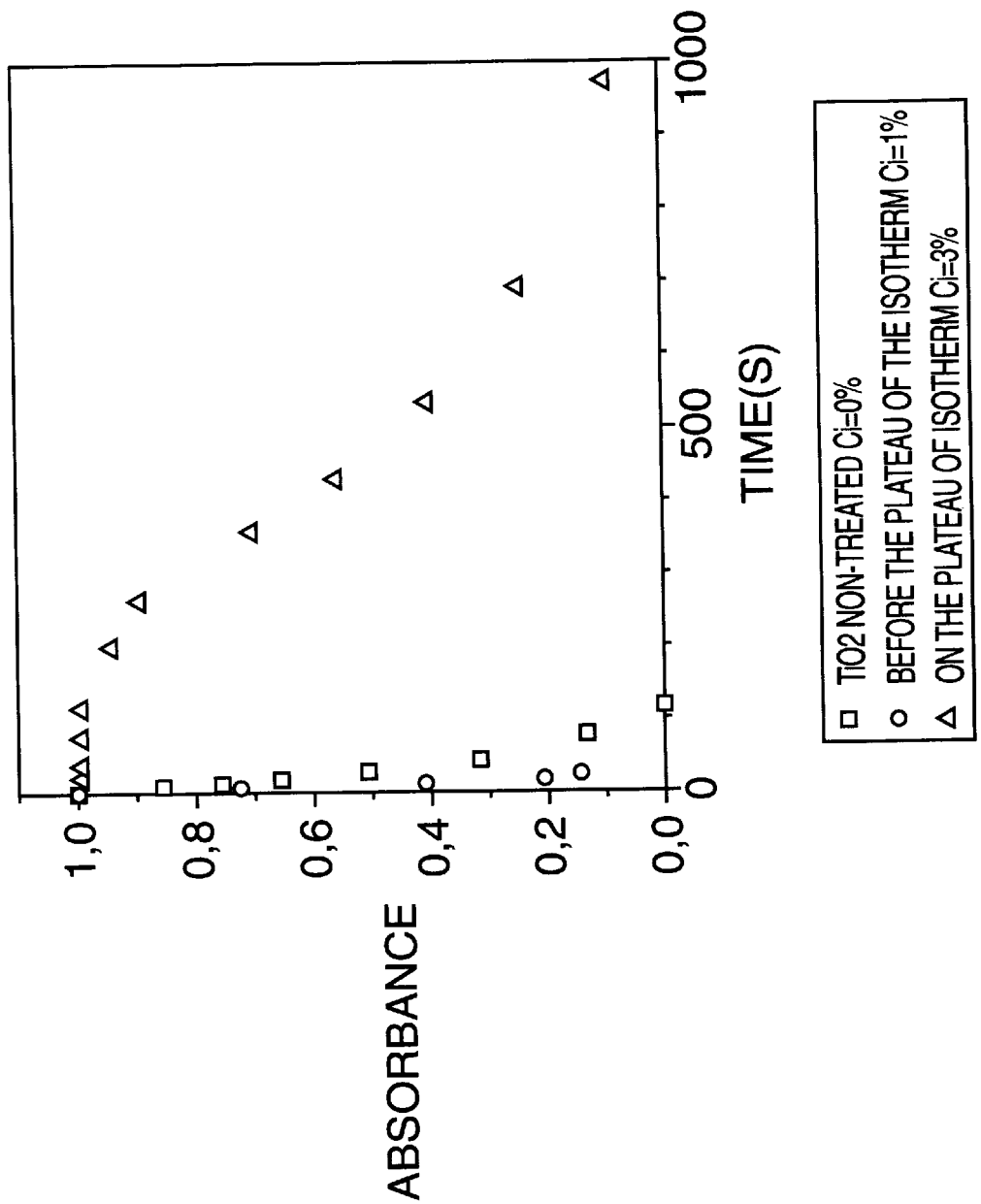
Figure 4:
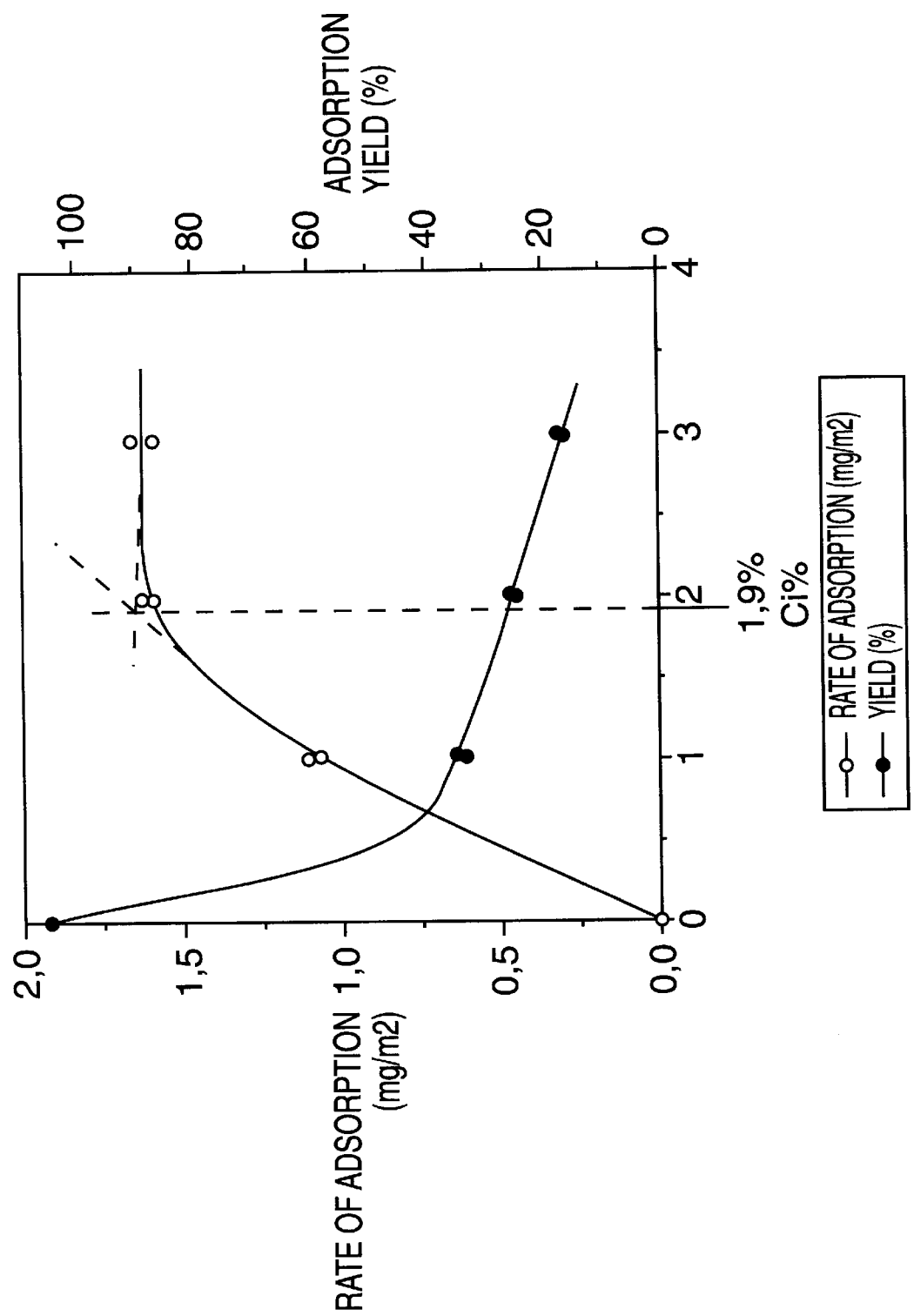
Figure 5A:
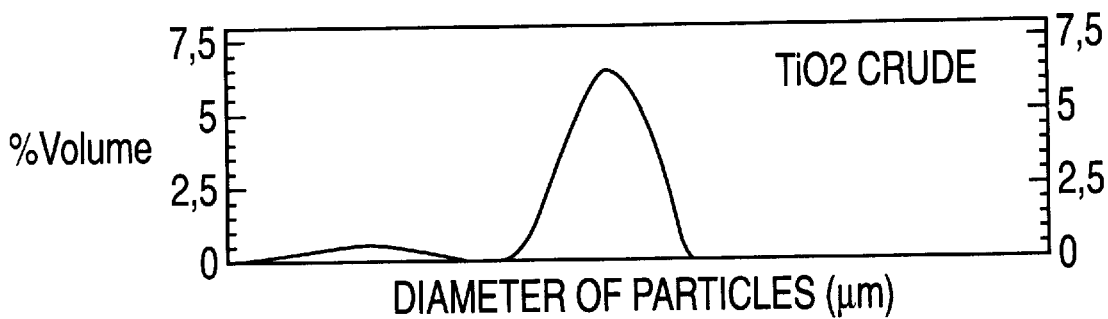
Figure 5B:
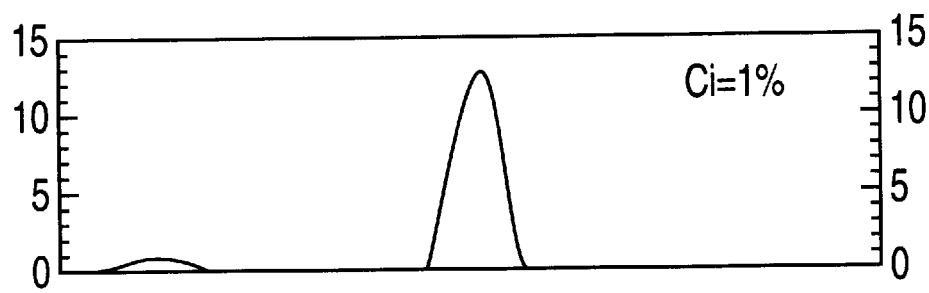
Figure 5C:
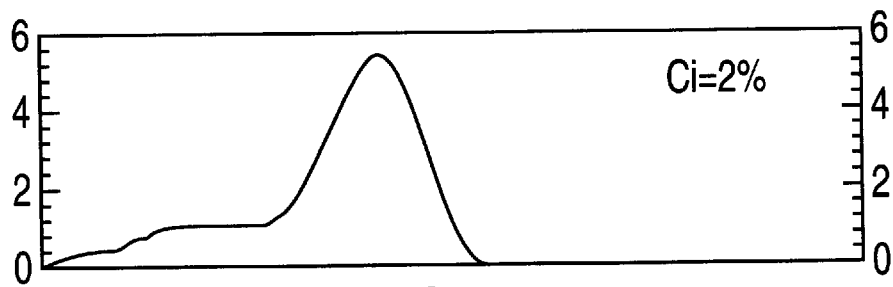
Figure 5D:
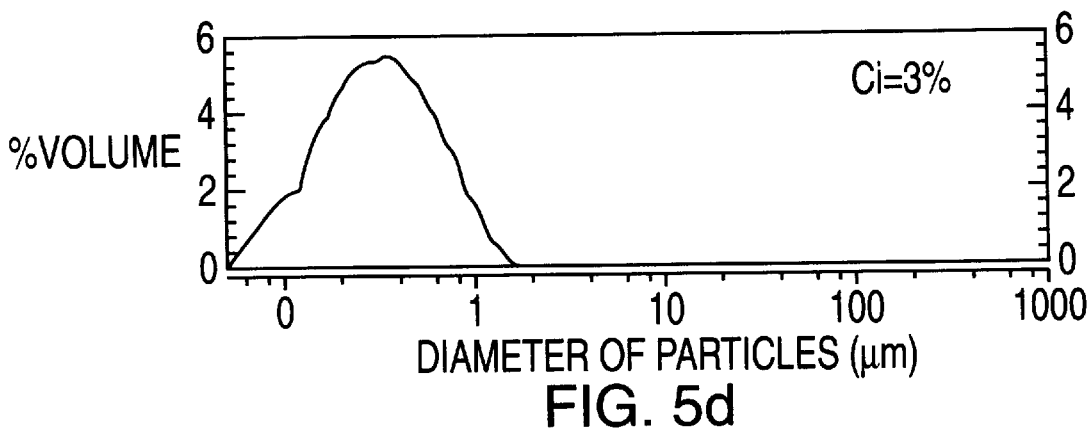
Figure 6:
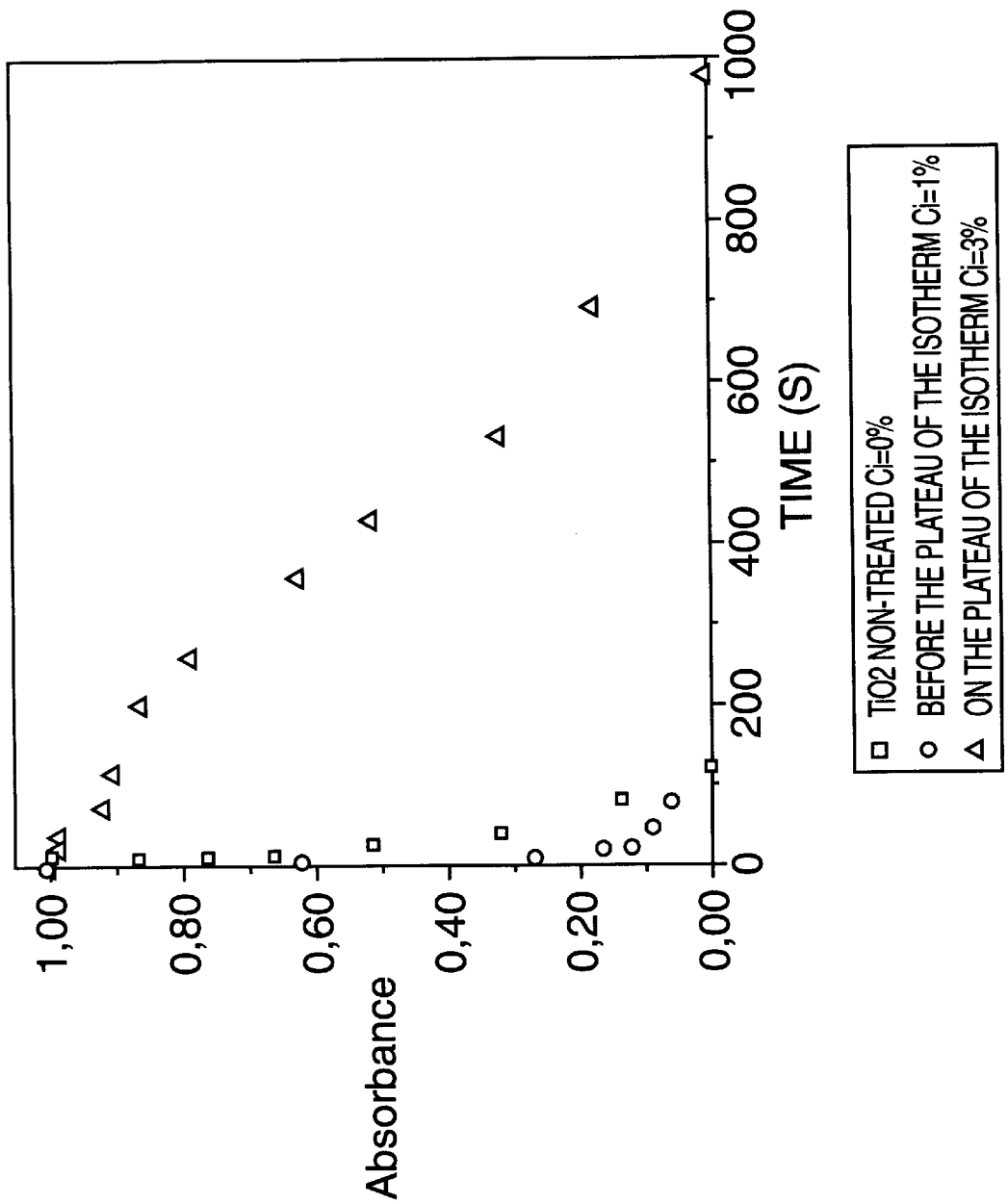
Figure 7:
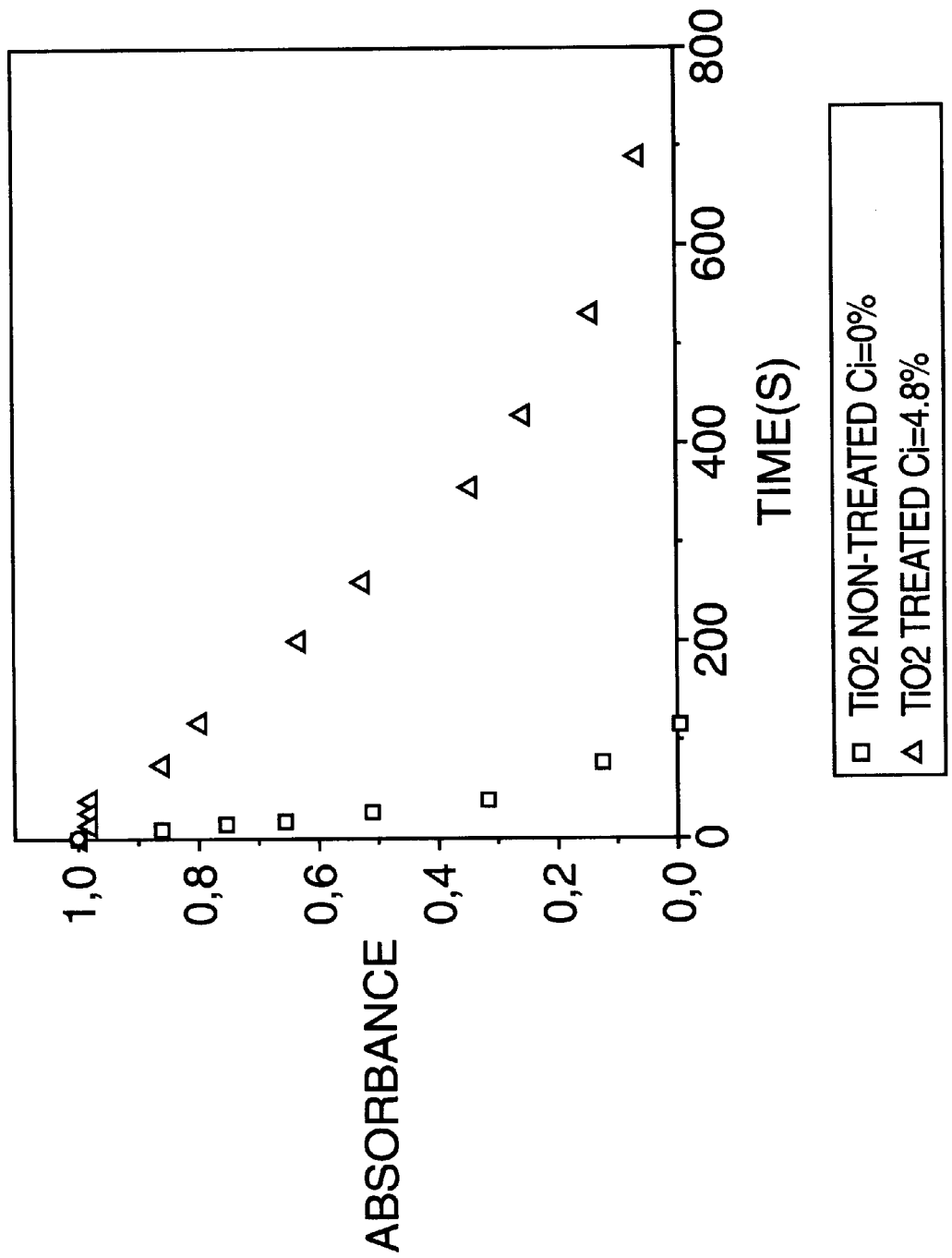
Figure 8:
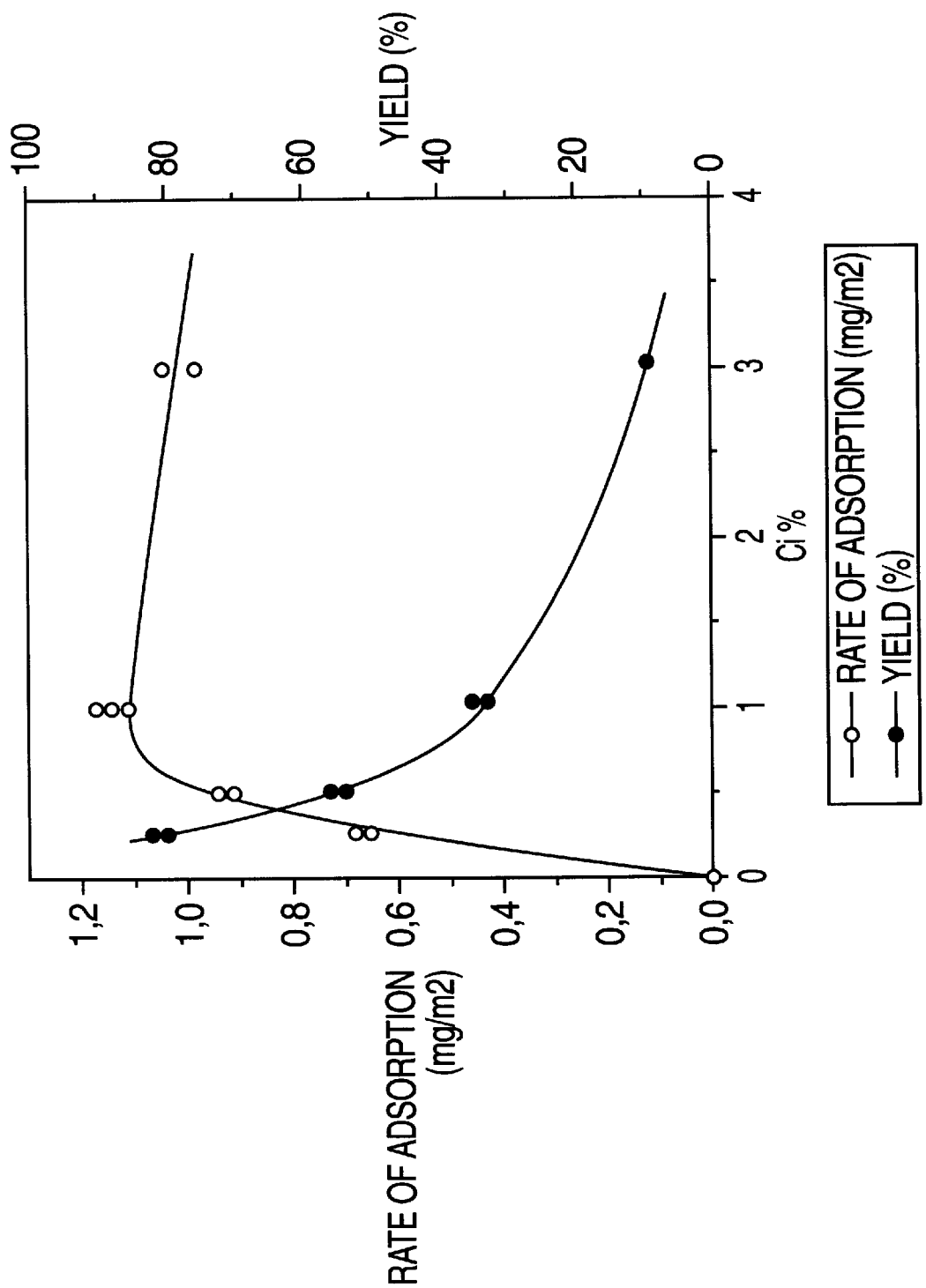
Figure 9A:
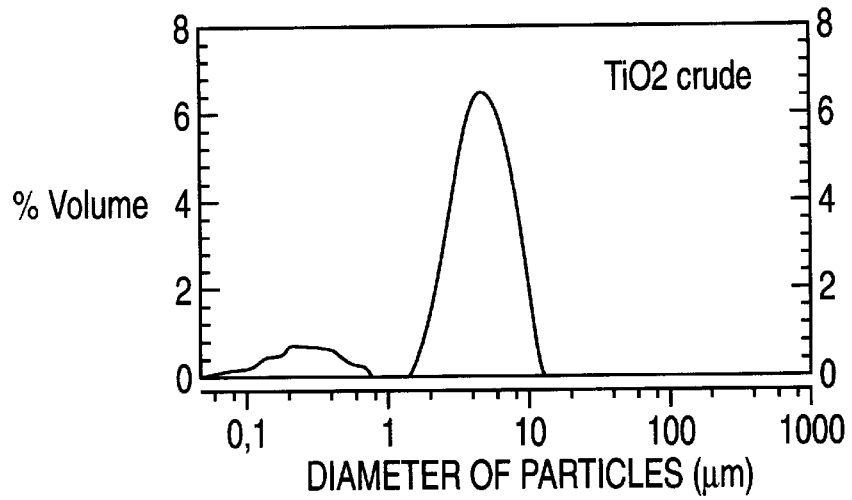
Figure 9B:
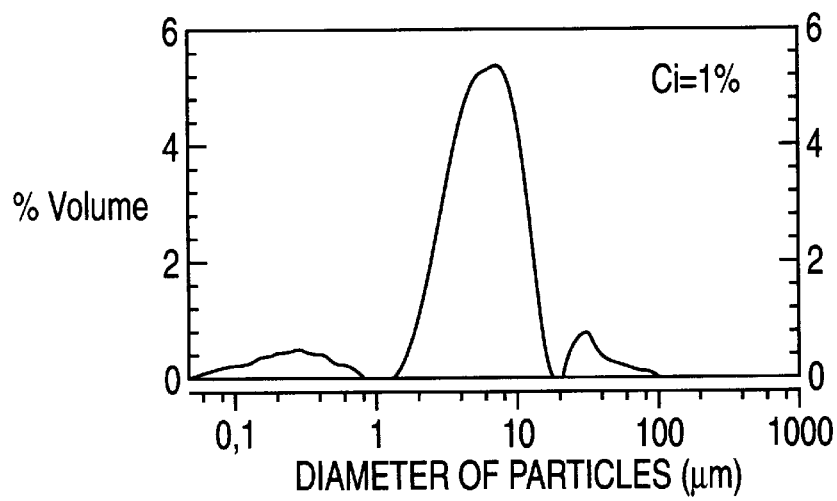
Figure 9C:
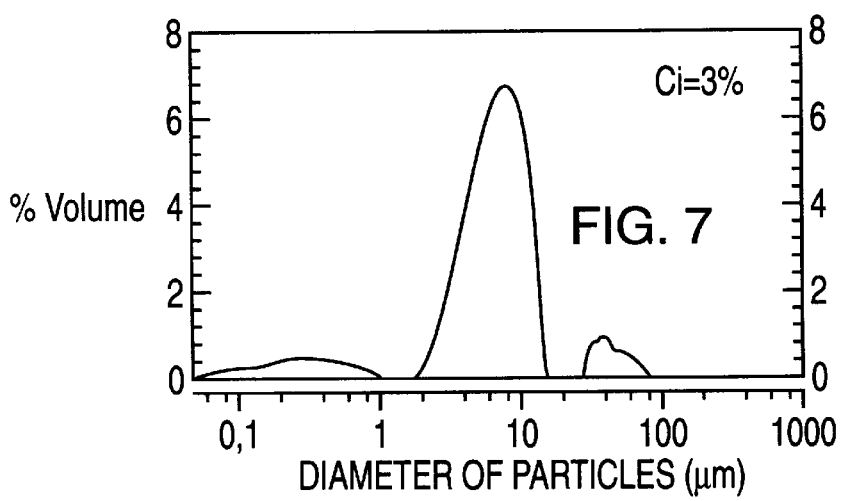
Figure 10:
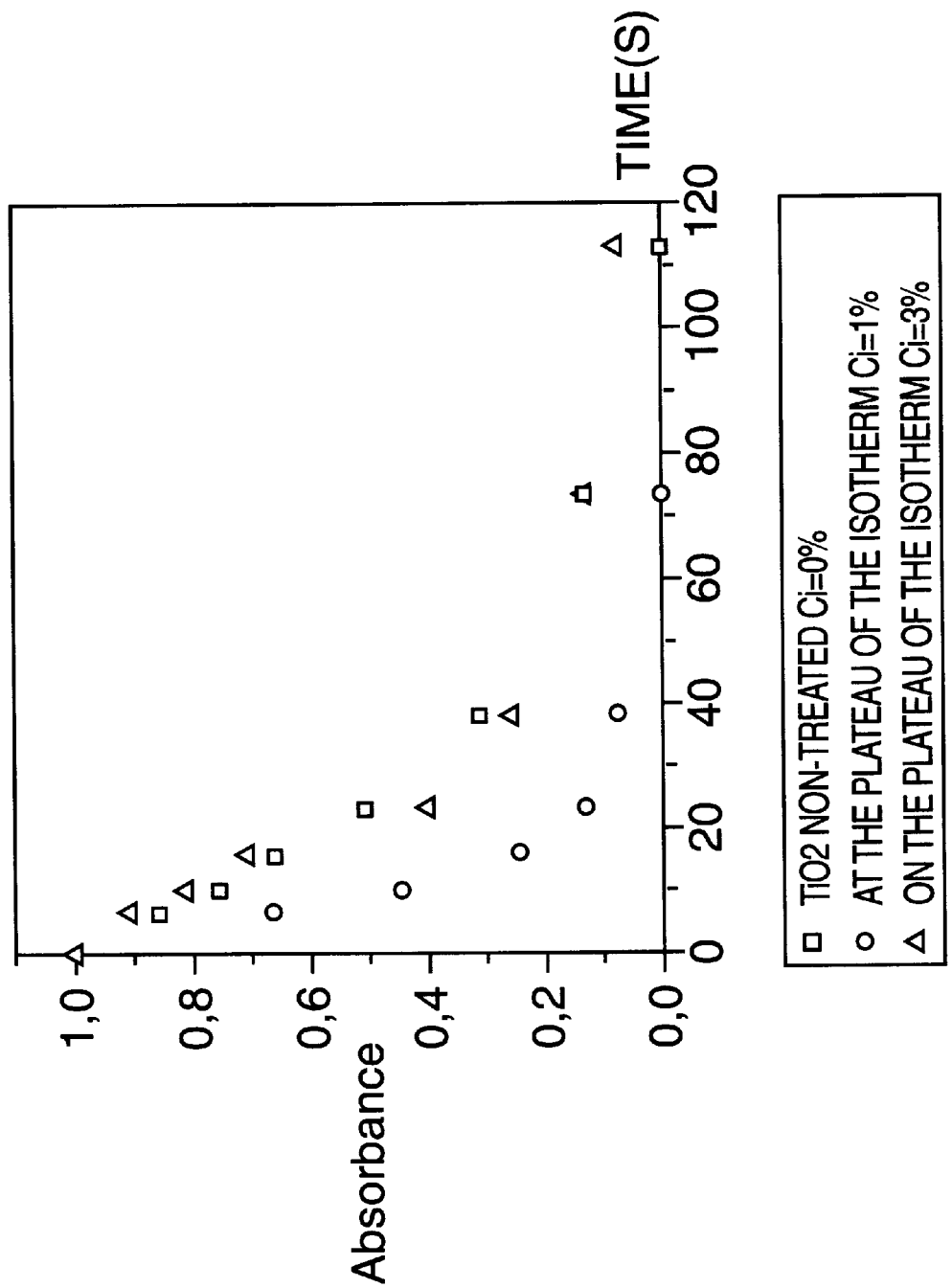

FIGS. 1, 2a to 2d, 3 are given with reference to Example 1 and relate more specifically to:

FIG. 1: the isotherm and the yield of adsorption of the functionalised polymer obtained in Example 1 on the $TiO_2$ powder in butyl acetate medium, FIGS. 2a, 2b, 2c, 2d: the results obtained by measuring, on the COULTER LS130, the dispersability of the same powder in the same medium for various initial concentrations of polymer obtained in Example 1, FIG. 3: the absorbance of the suspension against centrifugation time for the non-treated powder and in the presence of various concentrations of functionalised polymer obtained according to Example 1, FIGS. 4, 5a to 5d, 6 and 7 are given with reference to Example 2 and relate respectively to:

FIG. 4: the isotherm and the yield of adsorption of one of the polymers obtained according to Example 2 on the $TiO_2$ powder in butyl acetate medium, FIGS. 5a, 5b, 5c, 5d: the results obtained by measurement, on the CO ULTER LS130, of the dispersability of the same powder in the same medium for various initial concentrations of the same polymer, FIG. 6: the absorbance of the suspension against centrifugation time for the same non-treated powder and in the presence of various concentrations of the same functionalised polymer, FIG. 7: the absorbance of the suspension against centrifugation time for the same non-treated powder in the presence of various concentrations of the other functionalised polymer obtained according to Example 2, FIGS. 8, 9a, 9b, 9c and 10 are given with reference to Example 3 and more specifically relate to:

FIG. 8: the isotherm and the yield of adsorption of the non-functionalised polymer obtained in Example 3 on a $TiO_2$ powder in a butyl acetate medium, FIGS. 9a, 9b, 9c: the results obtained by measurement, on the COULTER LS130, of the dispersability of the same powder in the same medium for various initial concentrations of polymer obtained according to Example 3, FIG. 10: the absorbance of the suspension against centrifugation time for the non-treated powder and the same powder in the presence of various concentrations of non-functionalised polymer obtained in Example 3.

EXAMPLE 1

Ornithine-Functionalised Methyl Polymethacrylate 1.a. Synthesis 10 g of ornithine are dissolved in 39 g of water, 136 g of acetic acid are then added progressively.

The solution obtained is placed in a double cased reactor equipped with a stirring anchor, a condenser and a nitrogen circulation.

0.16 g of AIBN are dissolved in 10 g of MMA.

The whole is added to the preceding solution.

The whole is heated at 60° C. for 4 hours. After 2 hours and 30 minutes of polymerisation, a partial precipitation of the polymer is observed.

The precipitated product and that which has remained in solution are collected separately.

They are precipitated in n-butanol. Dried, optionally washed with water, they are then dissolved in acetone and reprecipitated in water.

Their number molecular mass is determined by GPC.

For the polymer precipitated during the polymerisation, Mn=87,500,

For the polymer which remained in solution during the precipitation, Mn=53,200.

1.b. Study of the influence of an ornithine-functionalised PMMA of Mn=87,500 on the dispersion of a titanium oxide powder in butyl acetate medium The powder used is a titanium oxide powder of 200 nm diameter and 10 $m^2/g$ specific surface.

The functionalised polymer of Mn=87,500 prepared in Example 1.a is placed in solution in butyl acetate at various concentrations. 3 g of $TiO_2$ are then added to 10 g of solution. Stirring is continued for 24 hours. The determination of the adsorption isotherms (rate of adsorption against the initial polymer concentration at 20° C.) enables obtaining the maximum rate of adsorption as well as the yield as shown in FIG. 1.

FIG. 1 gives the rate of adsorption (t) and the yield of adsorption (r) against the initial polymer concentration expressed in percentages by mass. The yield r is given by the relationship:

$$r=(Ci-Ce)/Ci \cdot 100 \, (100\%)$$

wherein Ci represents the initial concentration of functionalised polymer and Ce the concentration of the solution after placing the solution in contact with the solid particles and separation of the solid particles by centrifugation.

The rate of adsorption is given by $$t=[(Ci-Ce)m_s]/m_c S$$

wherein $m_s$ is the mass of solution and $m_c$ the mass of $TiO_2$ of specific surface S.

In the present case:

$m_s$=10 g

S=10 $m^2/g$ $m_c$=3 g

The line of the curve of FIG. 1 giving the rate of adsorption against the initial concentration Ci of functionalised polymer at 20° C. (adsorption isotherm) clearly shows the existence of a plateau on which the start of the line of the tangents is determined indicated in FIG. 1.

In the particular case of this example, the start of the plateau read on the curve corresponds to an initial concentration of functionalised polymer of 1.8% by mass, which corresponds according to the formula above to 60 mg of polymer for 1 g of $TiO_2$.

The dispersability is evaluated from the measurements of the sizes of particles with the aid of the COULTER LS130.

FIGS. 2a to 2d give the granulometric analyses of the $TiO_2$ correspond respectively to the Ci values of 0, 1, 2 and 3% for the same example as the adsorption isotherm. The functionalised polymer enables considerably reducing the aggregates until they disappear when the covering of the $TiO_2$ is total (i. e. for the initial polymer concentrations corresponding to the plateau of the isotherm).

For this type of example, a very good dispersing agent must reduce the quantity of aggregates to a value lower than 1% or at least considerably reduce their size.

The stabilisation is determined by varying the adsorbance of the supernatant in terms of the duration of the centrifugation of 120 $rpm/mn^2$ (Shimadzu SA-CP3).

FIG. 3 gives the absorbance of the suspensions against time respectively for the suspensions of non-treated $TiO_2$ (Ci=0%) as well as for concentrations Ci of 1% (before the plateau of the isotherm) and 3% (on the plateau of the isotherm).

When there is a decantation with time, the deposit formed remains easily redispersable in the medium after a more or less long period of stirring. The polymer totally covering the surface preventing the aggregation of the pigment.

In conclusion, 60 mg of functionalised polymer are necessary for dispersing and stabilising 1 g of $TiO_2$.

EXAMPLE 2

Glycine-Functionalised Methyl Polymethacrylate 2.a. Synthesis 10 g of glycine are dissolved in 39 g of water, 136 g of acetic acid are then progressively added.

The solution obtained is placed in a reactor similar to that used in Example 1.a.

0.16 g of AIBN are dissolved in 10 g of MMA.

The whole is added to the preceding solution.

The whole is heated at 60° C. for 3 hours. A partial precipitation of the polymer is observed during the reaction.

The precipitated product and that which remained in solution are collected separately.

They are precipitated in n-butanol. Dried, optionally washed with water, they are then dissolved in acetone and reprecipitated in water.

Their number molecular mass is determined by GPC.

For the polymer precipitated during the polymerisation, Mn=133,300.

For the polymer which remained in solution during the polymerisation, Mn=54,600.

2.b. Study of the dispersion of a $TiO_2$ powder in butyl acetate in the presence of a glycine-functionalised PMMA.

As in the preceding Example, the influence of the functionalised polymers obtained according to Example 2.a are studied on the dispersion of the same titanium oxide powder in butyl acetate.

FIG. 4 gives the rates of adsorption and the yield of adsorption against the initial concentration Ci of the functionalised polymer in the case of the glycine-functionalised PMMA of number average molar mass Mn=133,300 obtained according to Example 2.a.

It appears in FIG. 4 that the plateau of the isotherm of adsorption starts for concentrations Ci=1.9%. The calculation enables therefore establishing that 63 mg of functionalised polymer in the present case are adsorbed by 1 g of $TiO_2$.

The dispersability of the same $TiO_2$ in butyl acetate in the presence of various concentrations of the same functionalised polymer (Mn=133,300) was carried out by measuring the size of the particles on the COULTER LS130.

The results for the initial concentrations Ci of 0 (crude $TiO_2$), 1%, 2% and 3% are given respectively on curves 5a, 5b, 5c, 5d, which show clearly that the functionalised polymer enables considerably reducing the size of the aggregates until they disappear when the initial polymer concentrations correspond to the plateau of the isotherm ( from 1.9% in the present case).

FIG. 6 which gives the variation of the absorption of the suspensions of non-treated $TiO_2$ as well as for concentrations Ci of 1% (before the plateau of the isotherm) and 3% (on the plateau of the isotherm) of glycine-functionalised PMMA of number average molar mass of 133,300 clearly shows the effect of this polymer for stabilising the $TiO_2$ dispersion in butyl acetate.

In the case of the glycine-functionalised PMMA of Mn=133,300, 63 mg are therefore necessary for dispersing and stabilising about 1 g of $TiO_2$ in a butyl acetate medium.

FIG. 7 establishes in an analogous way to curve 6 but for the glycine-functionalised PMMA of Mn=54,600 also shows very clearly the stabilising effect of this product at an initial concentration Ci of 4.8%.

EXAMPLE 3

Non-Functionalised Methyl Polymethacrylate (comparative)

3.a. Synthesis 0.32 g of AIBN and 20 g of methyl methacrylate are dissolved in a mixture containing 136 g of acetic acid and 39 g of water.

The solution obtained is placed in a double cased reactor equipped with a stirring anchor, a condenser and a nitrogen circulation and is heated at 60° C. for 6 hours.

The collected mixture is precipitated in n-butanol so as to remove the remains MMA, MBN and its degradation products.

The number molecular mass of the polymer determined by GPC is Mn=92,400.

3.b. Effect of non-functionalised PMMA on the dispersion of a $TiO_2$ powder in a butyl acetate medium.

As a comparison, the effect of non-functionalised polymer obtained in Example 3a is studied on the dispersion of the same $TiO_2$ powder in a butyl acetate medium.

The curve represented in FIG. 8 represents the variations of the isotherm and the yield of the adsorption against the initial concentration Ci of the non-functionalised PMMA polymer. This curve, compared to the curves represented in FIGS. 1 and 4 for the functionalised PMMAs according to the invention, show that the plateau of the isotherm is situated at a lower value, corresponding to a Ci value of about 1%.

FIGS. 9a, 9b and 9c which give the results obtained by measuring, on the COULTER LS130, the size of the particles respectively for concentrations Ci of the polymer of 0, 1% and 3% clearly show that in the presence of non-functionalised polymer, there is by no means any dispersion but on the contrary rather an aggregation of the particles.

The curves of absorption of the suspension against time established for initial concentrations Ci of polymer of 0%, 1% and 3% also show that there is rather a destabilisation of the suspension in the presence of non-functionalised polymer and non-stabilisation.

EXAMPLE 4

Applications in Cosmetics Field—Nail Varnishes

In the Examples below, the percentages are given by weight, unless otherwise stated.

According to a prior art method well-known to the person skilled in the art, nail varnishes are prepared from <colouring solutions> of different tints, which are mixed with a base for nail varnishes. These <colouring solutions> are in fact dispersions of pigments in a base containing nitrocellulose, it being possible for this base to be the same as that used for the final formulation of the varnish. Preferably, the pigments are ground beforehand in a solvent, such as butyl acetate, by means of an appropriate grinder such as for example a ball grinder of the Dyno-mill type.

Following the present invention, the grinding of the pigment is carried out in the presence of the functionalised polymer according to the invention, used as agent which facilitates the dispersion of the pigment in the solvent.

Preferably, the proportion of polymer used is in the order of 2 to 7% with respect to the weight of the pigment. More preferably still, this proportion is about 5%.

Thus, the following grindings have been prepared:

| grinding n° 1: | | |
|---|---|---|
| Black iron oxide $Fe_3O_4$ | | 50% |
| Functionalised polymer of Mn = 87,500 according to Example 1 | | 2.5% |
| Butyl acetate | qs for | 100% |
| grinding n° 2: | | |
| Titanium oxide $TiO_2$ | | 70% |
| Functionalised polymer of Mn = 87500 according to Example 1 | | 2.8% |
| Butyl acetate | qs for | 100% |

-continued

| grinding n° 3 | | |
|---|---|---|
| Red Organic Pigment DC Red 7 | | 25% |
| Functionalised polymer of Mn = 87500 according to Example 1 | | 1.25% |
| Butyl acetate | qs for | 100% |

As it has been shown above, the grindings are incorporated into a <diluting> nitrocellulose base for preparing various colouring solutions, each one having its own tint according to the nature and the concentration of the pigment that it contains.

For example, the composition of the <diluting> base is the following:

| nitrocellulose | 10 to 30%, | for example | 15% |
|---|---|---|---|
| Lustralite ® (arylsulfonamide) | 8 to 15%, | for example | 10% |
| dibutyl-phthalate | 4 to 7%, | for example | 5% |
| Neocryl ® (acrylic resin) | 0 to 5%, | for example | 2% |
| butyl acetate | 5 to 50%, | for example | 20% |
| ethyl acetate | 5 to 50%, | for example | 20% |
| bentonite | 0.8 to 1.5%, | for example | 1% |
| toluene | 0 to 30%, | for example | 25% |
| isopropanol | 1 to 5%, | for example | 2% |
| | 100% | | 100% |

The amount of grinding introduced into the diluting base is such that the concentration of pigment in the colouring solution is generally lower than or equal to about 20%.

Following the desired tint of the final nail varnish composition, different colouring solutions at different concentrations are introduced into a base, such as the base above. The pigment content of the final nail varnish is generally in the order of 2 to 4%.

We claim:

1. Chain end functionalised polymer of formula:

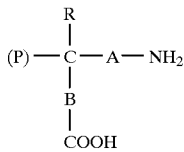

(1)

in which:
the polymer chain (P) is a hydrophobic chain obtained by radical polymerisation of at least one ethylenically unsaturated monomer,
R represents a hydrogen atom or a linear or branched hydrocarbon chain having 1 to 8 carbon atoms optionally substituted with at least one group selected from $CO_2H$, $NH_2$, OH or a phenyl group, itself being optionally substituted,
A and B, identical or different, each represent a single bond, a saturated or unsaturated linear or branched hydrocarbon chain having from 1 to 16 carbon atoms an amide bond or a peptide chain having 2 to 4 amino acids,
the COOH and/or $NH_2$ groups being free or salified.

2. Functionalised polymer according to claim 1, wherein the polymer chain (P) has a number average molar mass between 500 and 250,000.

3. Functionalised polymer according to one of claim 1 wherein said polymer is of formula:

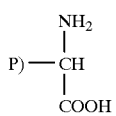

(3)

4. Functionalised polymer according to claim 1 wherein said polymers is of formula:

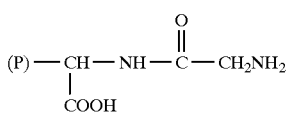

(4)

5. Functionalised polymer according to claim 1, wherein said polymer is of formula:

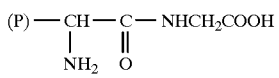

(5)

6. Functionalised polymer according to claim 1 wherein said polymer is of formula:

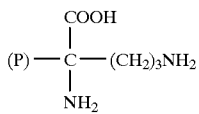

(6)

7. Functionalised polymer according to 1 wherein said polymer is of formula:

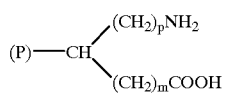

(7)

in which:
m and p are integers between 0 and 11 and whose sum is between 2 and 11.

8. Functionalised polymer according to claim 1 wherein said polymer it is obtained by radical polymerisation of at least one monomer in the presence of an amino acid of the formula:

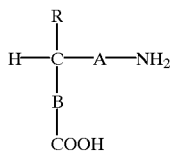
(2)

9. Functionalised polymer according to claim 7, wherein said polymer is obtained in a method comprising:
   a first step of radical polymerisation step of at least one monomer leading to a hydrophobic polymer chain P in the presence of a lactam acting as chain transfer agent and being of formula:

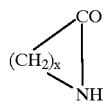
(8)

in which x is an integer between 3 and 12,
   followed by a second hydrolysis step of the product obtained during the first step.

10. Functionalised polymer according to claim 1 wherein said monomer is an acrylic or vinylic monomer.

11. Functionalized polymer according to claim 10 wherein said monomer is an acrylic monomer selected from the group consisting of acrylates, methacrylates, ethylacrylates of a saturated or unsaturated particularly allylic, linear, branched, or ring-containing C1 to C18 hydrocarbon group.

12. Functionalised polymer according to claim 1 wherein said polymer chain (P) results from the radical polymerisation of methyl methacrylate.

13. Intermediate product of the formula:

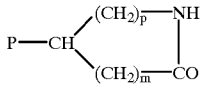
(9)

in which:
   (P) is a hydrophobic polymer chain resulting from the radical polymerisation of a monomer,
   p and m are integers between 0 and 11 and whose sum is between 2 and 11.

14. A method for dispersing solid particles in a liquid medium comprising the step of combining said particles with a chain end functionalised polymer of the formula:

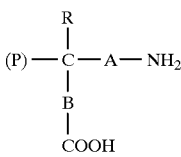
(1)

in which:
   the polymer chain (P) is a hydrophobic chain obtained by radical polymerisation of at least one ethylenically unsaturated monomer and whose number average molar mass is between 500 and 250,000;
   R represents a hydrogen atom or a linear or branched hydrocarbon chain having 1 to 8 carbon atoms optionally substituted with at least one group selected from $CO_2H$, $NH_2$, OH or a phenyl group, itself being optionally substituted;
   A and B, identical or different, each represent a single bond, a saturated or unsaturated linear or branched hydrocarbon chain having from 1 to 16 carbon atoms, an amide bond or a peptide chain having 2 to 4 amino acids;
   the COOH and/or $NH_2$ groups being free or salified.

15. A method for incorporating solid particles in a composition selected from the group consisting of paint, food, phytosanitary compositions and cosmetic compositions comprising the steps of combining said solid particles with a chain end functionalised polymer of the formula:

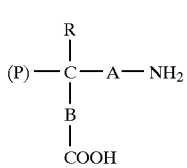
(1)

in which:
   the polymer chain (P) is a hydrophobic chain obtained by radical polymerisation of at least one ethylenically unsaturated monomer and whose number average molar mass is between 500 and 250,000;
   R represents a hydrogen atom or a linear or branched hydrocarbon chain having 1 to 8 carbon atoms optionally substituted with at least one group selected from $CO_2H$, $NH_2$, OH or a phenyl group, itself being optionally substituted;
   A and B, identical or different, each represent a single bond, a saturated or unsaturated linear or branched hydrocarbon chain having from 1 to 16 carbon atoms, an amide bond or a peptide chain having 2 to 4 amino acids;
   the COOH and/or $NH_2$ groups being free or salified; and
   adding said combined solid particles and functionalised polymer to said composition.

16. A surfactant having a formula:

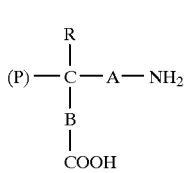
(1)

in which:
   the polymer chain (P) is a hydrophobic chain obtained by radical polymerisation of at least one ethylenically unsaturated monomer;
   R represents a hydrogen atom or a linear or branched hydrocarbon chain having 1 to 8 carbon atoms optionally substituted with at least one group selected from $CO_2H$, $NH_2$, OH or a phenyl group, itself being optionally substituted;
   A and B, identical or different, each represent a single bond, a saturated or unsaturated linear or branched hydrocarbon chain having from 1 to 16 carbon atoms, an amide bond or a peptide chain having 2 to 4 amino acids;

the COOH and/or $NH_2$ groups being free or salified.

17. A method to improve the wetting effect of a liquid medium towards a solid surface or particle comprising the step of adding to said liquid medium an effective amount of a chain end functionalised polymer of the formula:

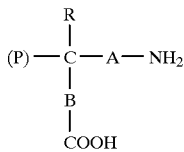
(1)

in which:
the polymer chain (P) is a hydrophobic chain obtained by radical polymerisation of at least one monomer;
R represents a hydrogen atom or a linear or branched hydrocarbon chain having 1 to 8 carbon atoms optionally substituted with at least one group selected from $CO_2H$, $NH_2$, OH or a phenyl group, itself being optionally substituted;
A and B, identical or different, each represent a single bond, a saturated or unsaturated linear or branched hydrocarbon chain having from 1 to 16 carbon atoms, an amide bond or a peptide chain having 2 to 4 amino acids;
the COOH and/or $NH_2$ groups being free or salified.

18. A method for forming an emulsion comprising the step of combining two liquids with a surfactant to form a liquid—liquid emulsion, said surfactant being a functionalized polymer of the formula:

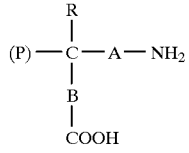

in which:
the polymer chain (P) is a hydrophobic chain obtained by radical polymerisation of at least one ethylenically unsaturated monomer,
R represents a hydrogen atom or a linear or branched hydrocarbon chain having 1 to 8 carbon atoms optionally substituted with at least one group selected from $CO_2H$, $NH_2$, OH or a phenyl group, itself being optionally substituted,
A and B, identical or different, each represent a single bond, a saturated or unsaturated linear or branched hydrocarbon chain having from 1 to 16 carbon atoms, an amide bond or a peptide chain having 2 to 4 amino acids,
the COOH and/or $NH_2$ groups being free or salified.

19. A method for incorporating solid particles in cosmetic compositions comprising the steps of combining said solid particles with a functionalized polymer of formula:

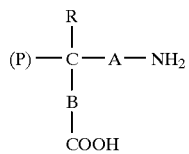

in which:
the polymer chain (P) is a hydrophobic chain obtained by radical polymerisation of at least one ethylenically unsaturated monomer,
R represents a hydrogen atom or a linear or branched hydrocarbon chain having 1 to 8 carbon atoms optionally substituted with at least one group selected from $CO_2H$, $NH_2$, OH or a phenyl group, itself being optionally substituted,
A and B, identical or different, each represent a single bond, a saturated or unsaturated linear or branched hydrocarbon chain having from 1 to 16 carbon atoms, an amide bond or a peptide chain having 2 to 4 amino acids,
the COOH and/or $NH_2$ groups being free or salified; and adding said combined solid particles and functionalized polymer to said composition.

20. A chain end functionalized polymer of formula:

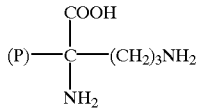

in which:
the polymer chain (P) is a hydrophobic chain obtained by radical polymerization of one ethylenically unsaturated monomer consisting essentially of methylmethacrylate, in the presence of ornithine.

21. The polymer of claim 20, wherein said polymer chain (P) has a number average molar mass Mn selected from the group consisting of about 87,500 and about 53,200.

22. A chain end functionalized polymer of formula:

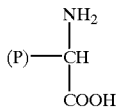

in which:
the polymer chain (P) is a hydrophobic chain obtained by radical polymerization of one ethylenically unsaturated monomer consisting essentially of methylmethacrylate, in the presence of glycine.

23. The polymer of claim 22, wherein said polymer chain (P) has a number average molar mass Mn selected from the group consisting of about 133,300 and about 54,600.

24. A method for forming an emulsion comprising the step of combining two liquids with a surfactant to form a liquid—liquid emulsion, said surfactant being a functionalized polymer as defined in claim 20.

25. A method for forming an emulsion comprising the step of combining two liquids with a surfactant to form a liquid—liquid emulsion, said surfactant being a functionalized polymer as defined in claim 22.

26. A method for incorporating solid particles in cosmetic compositions comprising the step of combining said solid particles with a functionalized polymer as defined in claim 20, and adding said combined solid particles and functionalized polymer to said composition.

27. A method for incorporating solid particles in cosmetic compositions comprising the step of combining said solid particles with a functionalized polymer as defined in claim 22, and adding said combined solid particles and functionalized polymer to said composition.

28. A cosmetic composition for the care or make-up of the nails, comprising a functionalized polymer as defined in claim 20.

29. A cosmetic composition for the care or make-up of the nails, comprising a functionalized polymer as defined in claim 22.

30. The method of claim 14 wherein said liquid medium is an organic medium.

31. The method of claim 14 wherein said functionalised polymer has a number average molecular mass greae than 1,000, and said liquid medium is an organic medium.

32. The method of claim 14 wherein said particles are selected from the group consisting of metallic oxide particles, metallic oxide covered with organic colorant molecules, and organic particles, coprecipitated with an organic colorant.

33. The method of claim 14 wherein said functionalised polymer has a number average molar mass lower than 20,000.

34. The method of claim 15 wherein said solid particles are pigments.

35. The method of claim 34 wherein said functionalised polymer is presence in an amount of between 2% and 7% by weight compared to the total weight of the solid particles in the composition.

36. The method of claim 15 wherein said functionalised polymer is a microdispersion of polymers.

37. The method of claim 36 wherein said microdispersion of polymers is present in an amount of between 1% and 20% by weight with respect to the total weight of the composition.

38. The method of claim 15 wherein the cosmetic composition is a nail varnish.

39. A cosmetic composition for the care or make-up of the nails, comprising a functionalised polymer of the following formula

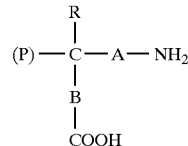

(1)

in which the polymer chain (P) is a hydrophobic chain obtained by radical polymerisation of at least one ethylenically unsaturated monomer and whose number average molar mass is between 500 and 250,000 and wherein R represents a hydrogen atom or a linear or branched hydrocarbon chain having 1 to 8 carbon atoms optionally substituted with at least one group selected from $CO_2H$, $NH_2$, OH or a phenyl group, itself being optionally substituted;

A and B, identical or different, each represent a single bond, a saturated or unsaturated linear or branched hydrocarbon chain having from 1 to 16 carbon atoms, an amide bond or a peptide chain having 2 to 4 amino acids;

the COOH and/or $NH_2$ groups being free or salified.

40. The cosmetic composition according to claim 39 wherein the functionalised polymer is a microdispersion of polymers.

41. The cosmetic composition of claim 39 further comprising nitrocellulose.

* * * * *